US008623278B2

(12) United States Patent
Reymond et al.

(10) Patent No.: US 8,623,278 B2
(45) Date of Patent: Jan. 7, 2014

(54) SYSTEM AND METHOD FOR THE CONTINUOUS EXTRACTION OF A LIQUID PHASE OF MICROSAMPLES, AND AUTOMATED INSTALLATION FOR TAKING THEM, FOR CARRYING OUT THE EXTRACTION AND TAKING MEASUREMENTS

(71) Applicant: Commissariat a l'Energie Atomique et aux Energies Alternatives, Paris (FR)

(72) Inventors: Jean-Marc Reymond, Saint-Remy-les-Chevreuse (FR); Sophie Kerhoas-Cavata, Raizeux (FR); Philippe Mangeot, Le Kremlin-Bicetre (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/649,639

(22) Filed: Oct. 11, 2012

(65) Prior Publication Data

US 2013/0035223 A1  Feb. 7, 2013

Related U.S. Application Data (62) Division of application No. 11/963,171, filed on Dec. 21, 2007, now abandoned.

(30) Foreign Application Priority Data

Jun. 19, 2007 (FR) ...................................... 07 04347

(51) Int. Cl.
G01N 21/00 (2006.01)
(52) U.S. Cl.
USPC ............... 422/63; 422/64; 422/65; 422/66; 422/67; 422/536; 436/180

(58) Field of Classification Search
USPC ............... 422/63–67, 500–503, 536; 436/180
See application file for complete search history.

(56) References Cited

U.S. PATENT DOCUMENTS

| 3,852,194 A | 12/1974 | Zine |
| 3,921,898 A | 11/1975 | Finkel |

(Continued)

FOREIGN PATENT DOCUMENTS

| EP | 0 688 993 | 12/1995 |
| EP | 1 450 159 | 8/2004 |
| FR | 2 395 037 | 1/1979 |
| WO | WO 00/21678 | 4/2000 |

OTHER PUBLICATIONS

Convert et al.; IEEE Transactions on Nuclear Science, vol. 54, No. 1; dated Feb. 2007; pp. 173.

(Continued)

Primary Examiner — Jyoti Nagpaul
(74) Attorney, Agent, or Firm — Alston & Bird LLP (57) ABSTRACT

A continuous automated extraction system and method for physically extracting at least one liquid phase of a series of liquid microsamples which are taken beforehand in discrete packets, both in space and in time, and are in stored is provided. The method may include an extraction system having a centrifuge provided with a plurality of microholders, at least one of which is filled with the corresponding microsample and includes a filling upper portion that is extended by a separating lower portion of smaller cross section than that of the upper portion. Each filled microholder has a mass which is more than ten times the mass of this microsample, in such a way that it is possible to extract, by centrifugation, at a given instant, only a single microsample contained in a single microholder, or several microsamples contained in some or all of these microholders, progressively as the latter are filled.

10 Claims, 8 Drawing Sheets

(56) References Cited

U.S. PATENT DOCUMENTS

| | | | |
|---|---|---|---|
| 4,386,120 A | | 5/1983 | Sato et al. |
| 4,683,120 A | * | 7/1987 | Meserol et al. ............... 422/72 |
| 5,338,689 A | | 8/1994 | Yves et al. |
| 5,389,339 A | * | 2/1995 | Petschek et al. ............... 422/64 |
| 5,399,144 A | | 3/1995 | Romanauskas et al. |
| 5,906,744 A | | 5/1999 | Carroll et al. |
| 6,254,834 B1 | | 7/2001 | Anderson et al. |
| 2003/0199789 A1 | | 10/2003 | Boecker et al. |
| 2004/0166551 A1 | | 8/2004 | Moulds |
| 2005/0026765 A1 | | 2/2005 | Escal |
| 2007/0083160 A1 | | 4/2007 | Hall et al. |

OTHER PUBLICATIONS

Lin et al.; "Automatic Control System of a Microfluid Blood Sampler for Quantitative microPET Studies in Small Laboratory Animals;" IEEE Nuclear Science Symposium Conference Record, dated 2006.

Lapointe D et al: "A Microvolumetric Blood Counter/Sampler for Metabolic PET Studies in Small Animals"; Aug. 1998; IEEE Transactions on Nuclear Science, IEEE Service Center, New York, NY; pp. 2195-2199, XP011088175.

Search Report from priority document French Patent No. 07/04347, filed Jun. 19, 2007.

* cited by examiner

SYSTEM AND METHOD FOR THE CONTINUOUS EXTRACTION OF A LIQUID PHASE OF MICROSAMPLES, AND AUTOMATED INSTALLATION FOR TAKING THEM, FOR CARRYING OUT THE EXTRACTION AND TAKING MEASUREMENTS

FIELD AND BACKGROUND OF THE INVENTION

The present invention relates to a system and a method for the continuous automated physical extraction of at least one liquid phase of a series of liquid microsamples which are taken beforehand as discrete packets in space and in time and are stored, and to an automated installation for carrying out, in succession and continuously, the taking of such microsamples, in storing them and in extracting at least one phase thereof and optionally measurements thereof. The invention applies more particularly, but not exclusively, to whole blood microsamples taken from a mammal, such as a rat or a mouse.

It is known to use centrifugal force to separate the various phases or components of liquid microsamples, such as whole blood from mammals, in biology, for the purpose of physically extracting, by centrifuging, at least one phase of these microsamples. However, the high speed of rotation that characterizes current centrifuges prevents them in practice from operating when their charge is not balanced, i.e. when all the microsamples are not placed at locations intended to accommodate them during this rotation, which typically consist of microcontainers housed in the centrifuge.

In the case of whole blood microsamples, various techniques are used to collect, filter and then separate the whole blood into constituents of different densities. It is general practice to use a micropipette and microcontainers that may already be in place in the centrifuge and that are filled in turn until the complete filling capacity of the centrifuge has been reached. The latter is then made to undergo rapid rotation, for a suitable time, so that the various components of the blood (such as serum/plasma on the one hand, and red corpuscles on the other) are separated inside each microcontainer.

For example, mention may be made of document US-A-2004/0166551 which has a centrifuge in which the microcontainers are holders each having an upper portion for being filled with the microsample, said portion being extended, via a narrowing in its cross section, by a lower portion for separating the constituents of this microsample, such as blood.

It is also known to use an extraction agent facilitating this separation within total blood microsamples, the density of which is intermediate between that of the various phases of the blood and which consists of a polymer gel. For example, mention may be made of document U.S. Pat. No. 5,906,744 for the use of such an extraction gel, which is by nature thixotropic.

When blood microsamples are sequentially transferred to such microcontainers for the centrifuge, there arises, apart from the problem of the uncertainty in the volume precision due to the micropipette used for the transfer, the aforementioned problem, which lies in the need to fill all of the microcontainers with microsamples in order to carry out the centrifugation, thereby preventing the microsamples from being centrifuged progressively as they are transferred into these microcontainers owing to the imbalance (i.e. the lack of balancing of the load in the centrifuge). In general, the smallest filling volume used in a centrifuge accommodating these microcontainers is about 200 µl.

Another major drawback of known centrifugation extraction systems and methods for blood microsamples is that an operator is normally required for sequencing the operations of taking these microsamples from the mammal in question and then temporarily storing them, followed by the operations of transferring the microsamples taken and stored into the microcontainers of the centrifuge in order to carry out the centrifugation.

The main automated systems known for taking blood microsamples derive from the field of molecular imaging in preclinical research on small mammals. In particular, to measure the concentration of an endogenous molecule, an imaging technique known as positron emission tomography (PET for short) is used, via the pharmacokinetic modeling of a radiotracer administered intravenously. In practice, the radiotracer concentrations are measured by this technique over the course of time at various points in the organism, called "organs", and in the compartment that delivers the radiotracer to all the organs, that is to say the arterial blood. The tomographs for small animals are used to extend the field of PET to preclinical trials in rodents, and to make diagnostic and therapeutic research benefit from this technique. On the down side, it becomes difficult to measure the arterial fraction by the usual blood sampling methods. This is why micromethods have been developed for measuring PET radiotracers in small animals, especially rats and mice.

A first micromethod of measurement was developed by a group of Canadian research workers at Sherbrooke University, for the purpose of continuous automatic sampling. In small animals (rats and mice), this group thus developed a system (see the article by Convert et al., IEEE Transactions on Nuclear Science, Vol. 54, No. 1, February 2007, 173) commercialized by the company AMI (Advanced Molecular Imaging)/Gamma Medica. To summarize, in this system the blood is continuously extracted from the animal using a pull-syringe but no collecting of samples is possible. This has the drawback of not meeting the requirements of new tracers that require the subsequent recovery of blood samples.

It may be noted that the same group had developed in 1998 (see the article by D. Lapointe et al. "A Microvolumetric Blood Counter/Sampler for Metabolic PET Studies in Small Animals", IEEE TRANSACTIONS ON NUCLEAR SCIENCE, VOL. 45, No. 4, AUGUST 1998) a system for extracting 10 µl blood samples and taking them automatically into a positron-sensitive counter. The computer-controlled blood sampler was based on a segmentation of the blood microsamples by air microbubbles (1 to 3 µl). At the end of the experiment, the tube thus formed could be cut, thus making the microsamples available for subsequent biochemical analysis. The treatment of these specimens has the drawback of not being able to be carried out automatically on the sampling line.

A second measurement micromethod was developed by a group of American researchers (Department of Molecular and Medical Pharmacology, UCLA School of Medicine & Department of Molecular and Medical Pharmacology) and relates to the automated taking of samples and their collection. The reader may usefully refer to the article by Huong-Dun Lin et al., Automatic Control System of a Microfluidic Blood Sampler for Quantitative microPET Studies in Small Laboratory Animals, 2006 IEEE Nuclear Science Symposium Conference Record), which describes a blood sampling system on a microfluidic chip that collects blood samples of small volume (180 nl) with an adjustable sampling time. In this system, the minimum time between two samples is 2 seconds and the amount of liquid deposited depends on the precision of the micropipette. In this microfluidic chip, only 18 blood samples could be collected.

The preliminary results have allowed blood kinetics to be derived with the "FDG" radiotracer on mice. Since the total blood loss is less than 3.5 µl, the impact on the physiological change is reduced to a minimum. On the down side, it is necessary to wait until the sampling procedure has been completed for the blood samples to be rinsed off the chip and into microtubes before then being counted in a gamma detector of the "well" type. Although this constraint is not very detrimental at the start of an entry function, in which the first samples are taken very close together, the same does not apply in the case of the last samples which are much more spaced apart and for which the time interval continues to increase. Thus, the gamma counting of the first of the 18 samples is carried out a very long time after it was taken. Since in addition the activity to be measured itself decreases strongly, the signal-to-noise ratio becomes very degraded.

Other drawbacks of this second method lie in the relatively long minimum sampling time between samples, being 2 seconds, and by the fact that the radiotracer counting on whole blood is carried out only at the end of a sequence (a minimum of 1 h after injection), which makes this method difficult to implement for tracers such as $^{11}$C which has a half-life of 20 minutes (there remains only one-eighth of the amount of tracer after 1 h, since this is equivalent to three half-lives). Furthermore, this rapid decrease in the quantity to be measured is considerably accentuated by the difficulty in separating the plasma (containing the radiotracer) from the corpuscles. Specifically, for sample volumes of 0.18 µl sufficient separation for carrying out differentiated measurements in line may even be considered to be impossible.

SUMMARY OF THE INVENTION

One object of the present invention is to provide a continuous automated extraction system for physically extracting at least one liquid phase of a series of liquid microsamples, comprising a centrifuge provided with a plurality of microholders, at least one of which is filled with the corresponding microsample and includes a filling upper portion that is extended by a separating lower portion of smaller cross section than that of the upper portion, which system remedies all the aforementioned drawbacks.

For this purpose, an automated extraction system according to the invention is such that said or each holder thus filled has a mass which is more than ten times the mass of this microsample, in such a way that it is possible to extract, by centrifugation, at a given instant, only a single microsample contained in a single microholder, or several microsamples contained in some or all of these microholders, progressively as the latter are filled.

The term "microsample" is understood in the present description to mean liquid samples, such as blood samples, each having a volume of less than 100 µl and preferably equal to or less than 30 µl (i.e. typically samples taken from small mammals, such as rats or mice).

Advantageously, said or each microholder thus filled has a mass that is more than 100 times the mass of this microsample.

It should be noted that these features testify to the fact that, according to the present invention, the mass of the microholders used in the centrifuge is not significantly modified by the liquid microsamples that they contain. This advantageously makes it possible to centrifuge a single microsample or only a few microsamples depending on the charging of the centrifuge, without having to wait for all the microholders that may be housed in the centrifuge to be filled beforehand with microsamples, as in the prior art.

According to another feature of the invention, said portions of each microholder preferably have substantially identical volumes, each volume being intended to contain in practice one microsample.

Again as a preference, said centrifuge may be provided with means for measuring the level of the microsample in said upper portion of each microholder that is filled therewith, such as photodetectors, so as to be able to remove the overflow of the microsample in this upper portion while said holder is being filled.

It should be noted that, because of the approximately identical volumes that characterize these two portions of the microholder, it is thus possible to regulate at will the volume of each microsample in the lower portion following its introduction into the upper portion and the centrifugation of the microholder. As a variant, this volume adjustment may be carried out by mechanically "leveling off" the microsample in the upper portion, should there be an overflow into the latter.

According to one particularly advantageous embodiment of the invention, each microholder of said centrifuge may further contain, before it is filled with the corresponding microsample, at least one extraction agent which is capable of extracting said phase from the microsample and the density of which is chosen to be intermediate between that of said phase and that of the remainder of the microsample in such a way that, during centrifugation, this agent migrates to the interface between said phase and the remainder of the microsample, forming a physical barrier thereat.

It should be noted that the incorporation of this extraction agent into each microholder makes it possible for the mass of the latter to be modified even less after it has been filled with the corresponding microsample.

Advantageously, said extraction agent comprises a MAGIC (Methacrylic and Ascorbic acid in Gelatin Initiated by Copper) polymer gel.

The extraction system according to the invention may further include a micropipette which is designed to transfer a specified amount of said extraction agent into each microholder and is mounted so as to move on an articulated arm.

According to another feature of the invention, the extraction system according to the invention may further include transfer means which are mounted so as to move on an actuating member and are intended to transfer, via a metering pump such as a peristaltic pump, a specified volume of each microsample from a storage container to at least one of the microholders waiting to be filled. These transfer means may comprise a micropipette and an articulated arm for actuating it, which are identical to or different from said micropipette and said arm that are intended to transfer said extraction agent.

According to another feature of the invention, this extraction system advantageously includes a computer-aided control device which is in particular capable of controlling said transfer means and their actuating member, the operation of said centrifuge and means for ejecting the microholders (i.e. extraction from the centrifuge).

Advantageously, if it is wished to make the centrifuge rotate with only a few microsamples, then these will not be placed in consecutive microholders but distributed in a balanced manner in this centrifuge.

Advantageously, each microsample contained in the corresponding microholder may be a whole blood microsample from a mammal having a volume of between 1 µl and 100 µl, for example about 8 µl in the case of a mouse blood microsample or equal to 30 μl in the case of a rat blood microsample. Said phase to be extracted from each microsample may then be blood plasma that said system separates from cells of the blood, such as red corpuscles.

It will be noted that this continuous extraction system according to the invention makes it possible in particular to separate, spatially and automatically, the corpuscles contained in the whole blood and that it is applicable to the particular case of nuclear imaging which requires the radiotracer activity of the blood plasma to be measured in line.

However, it will be noted that the invention potentially covers a much wider field, relating to taking of liquid microsamples, for example of a two-phase liquid, the discretization of the samples and, for each of them, the physical separation of at least one of its constituents, by having a higher or lower density than that of the other constituents. The intended purpose of this extraction may be to apply different actions to these microsample parts, which actions, given the volumes in question, are typically but not necessarily radiative counting or analysis, without excluding this purpose from for example the nanofluidic field.

A continuous automated extraction method according to the invention for physically extracting at least one liquid phase of a series of liquid microsamples, such as whole blood microsamples from a mammal, which are taken beforehand in discrete packets, both in space and in time, and are stored, is carried out by the extraction system of the invention described above. This method comprises the use of at least one microholder filled with a microsample and having a mass that is more than 10 times and preferably more than 100 times the mass of this microsample, and the control, by a computer-aided control device, of the centrifuge, a metering pump (for example a peristaltic pump) placed upstream of this centrifuge and means for inserting and ejecting the microholders, in such a way that it is possible, at a given instant, to carry out the extraction by centrifuging all or some of the microholders, progressively as the latter are filled.

According to the particularly preferred embodiment of the invention, this extraction method comprises, before each microholder is filled, the incorporation into the latter of an extraction agent which is capable of extracting said phase from the microsample and the density of which is chosen to be intermediate between that of said phase and that of the remainder of the microsample in such a way that, during the centrifugation, this agent being initially located in said upper portion and then, by centrifugation, in said lower portion of each microholder in order to migrate to the interface between said phase and the remainder of the microsample, forming a physical barrier thereat, this agent preferably being said MAGIC polymer gel.

According to a preferred embodiment of the invention, the following steps are carried out in succession during the centrifugation of each microholder:

a) each microholder is filled with this extraction agent, which is then located in the upper portion;

b) each microholder containing this extraction agent is centrifuged, said agent passing from the upper portion to the lower portion;

c) each microholder thus obtained is filled with a microsample in said upper portion; and then d) each microholder is centrifuged for the aforementioned extraction.

It should be noted that even in the absence of extraction agent in each microholder, the microsample advantageously remains in said upper portion during the filling operation, owing to its relatively high viscosity (especially in the case of a blood microsample). In the event of an excess of microsample in this upper portion, the overflow may be removed, for example by mechanical "leveling off" or via the aforementioned detection means.

Advantageously, the incorporation of said extraction agent in each microholder to be filled may be carried out by displacement of a micropipette actuated by an articulated arm introducing, into each microholder, a specified constant amount of this agent, and then by the rotation of said centrifuge until said agent falls to the bottom of this microholder.

The method of the invention further includes, before the extraction, a transfer of a specified volume of each microsample from a storage container to at least one of the microholders that has not yet received a microsample, advantageously via the displacement of a micropipette mounted on an articulated arm.

For example, the same micropipette as that transferring said agent may be used for transferring the microsamples.

According to another feature of the invention, prior to this extraction:

a) the microsamples are continuously taken, by an automated sampling system, according to a monotonic time function, via the sending at preprogrammed instants $t_i$, by said control device, to this sampling system, of signals for the taking of a microsample $e_i$ of preprogrammed volume; and then b) these microsamples $e_i$ thus taken follow one another spatially and temporally in a temporary storage line as far as a downstream end of this line where each microsample drops into a receptacle from where it is then continuously transferred, via said metering pump which is preferably a peristaltic pump, into the microholders of said centrifuge, the synchronism between this transfer and the progression of the microsamples in this storage line being controlled by this computer-assisted control device.

It should be noted that the minimum sampling time for the continuous sampling method of the invention is advantageously one second. This represents half the sampling time used in the prior art, as indicated above.

An automated installation according to the invention for carrying out, in succession and continuously, the taking of liquid microsamples as discrete packets in space and in time, their storage and the extraction of at least one phase thereof, comprises:

a continuous automated sampling system for taking microsamples via a peristaltic pump, for sucking up these microsamples in bursts, and for temporarily storing said microsamples;

the extraction system according to the invention, which is placed downstream of this sampling system by means of said metering pump which is preferably a peristaltic pump, in which said microholders each have a diameter in their upper portion that is equal to or larger than the diameter of their lower portion, the former diameter being for example twice the latter diameter; and a computer-aided control device for controlling all these systems and said pump.

Advantageously, each microholder has a height equal to or greater than 30 mm and is provided, in its upper portion, with a measurement apparatus for measuring a physical quantity relating to radiation to which the wall of each microholder is transparent, which apparatus, such as a gamma-radiation well counter or a fluorescence counter, is placed on the same axis as this microholder.

Advantageously, each liquid microsample coming from said extraction system and subjected to this measurement then consists of whole blood in which the plasma has been separated from the corpuscles, this measurement apparatus being an absolute gamma counter of the well-counter type, which is designed to measure the activity of just the plasma of each microsample, through the corresponding microholder, or else just the corpuscles thereof Even more advantageously, said counter and a computer-controlled robotic push-rod are then placed respectively above and below a location in the centrifuge intended to accommodate each microholder which is to undergo this measurement, the robotic push-rod being capable of momentarily pushing each microholder so as to bring its upper part into a shield for the counter, in order to measure the activity of just the plasma, the blood corpuscles deposited by centrifugation on the bottom of each microholder remaining outside this shield.

According to another feature of the invention, this automated sampling system may advantageously have a succession of lines through which the microsamples pass, the cross-sectional enlargements of said lines all being less than or equal to 20% in terms of area ratios, in such a way that the microsamples in discrete packets both in space and in time that follow one another in this succession of lines, in particular those having a volume of 30 µl or less, do not in practice become mixed together.

According to another feature of the invention, said automated sampling system comprises an upstream fluid connection device which is intended for transferring a liquid, such as blood microsamples, to be taken, which system is intended to be connected to a first line via a first opening in the connection device, which includes a second opening through which a second line passes, the second line being intended to communicate with the first line in order to transfer this liquid. Advantageously, this first line is a flexible microtube catheter suitable for taking blood microsamples from a small animal, such as a rat or mouse, the catheter being preferably implanted in the caudal vein of the animal to this end.

This connection device comprises:
 a female fluid connector that defines said first opening into which said first line is intended to be pushed and has an internal fitting surface terminating in a female radial end into which this first line opens; and
 a male fluid connector that defines said second opening, which is fitted into the female connector via its external surface and terminates via its male radial end inside the female connector.

According to the invention, the connection device is such that this second line is formed from a flexible microtube which is pushed right through the male connector axially beyond said male end, the free end of this second line pressing in a sealed manner against said female end so as to minimize the dead volume between the first line and the male connector.

It should be noted that this dead volume minimized by the connection device according to the invention makes it possible to remedy the drawbacks associated with the flow of microsamples—typically having volumes of 30 µl or less—in the known connection devices, these being in particular a delayed passage of the first microsamples, loss of liquid volumes taken, and potential mixing of the microsamples impairing their traceability in particular).

According to another feature of the invention, said internal fitting surface of the female connector may be a conical surface converging on said female end with the same conicity as said external surface of the male connector, which converges on said male end. Preferably, said male and female connectors may both then be connectors of the "Luer" type, as defined by the ISO 59461 standard of 1986, or else of the "Luer-lock" type, as defined by the ISO 594-2 standard of 1998.

Preferably, said second line may extend beyond said male end by an axial length at least equal to the minimum distance separating said respective ends of the two connectors when the male connector is pushed right into the connection position in the female connector in accordance with one or other of said standards.

Also preferably, said second line is provided, around its cylindrical wall and near its free end, with a stiffening means capable of stiffening it inside said female connector.

Advantageously, said stiffening means is formed from a ring made of a material that has a stiffness at least equal to and preferably greater than that of said second line and is capable of being fastened thereto, it being possible for this fastening to be direct or via said male fluid connector. In the latter case, the male fluid connector is necessarily fastened to said second line.

According to a preferred variant, the stiffening means is fastened to the end of the second line, which it clamps, and is mounted so as to bear between the latter and said conical internal fitting surface of the female connector. As an example, this stiffening means may be based on a polymeric resin.

This ring may be attached around the second line or else coextruded with the latter. According to a variant more suitable for industrial production, the male connector may be produced in a single molding operation, after a slight remachining of the initial shape of the mold allowing the incorporation of this stiffening means.

This second line may for example be made of a material based on a low-density polyethylene (LDPE), for example in order to minimize the absorption of beta-radiation for the purpose of particle counting carried out downstream of this device.

As regards the succession of lines of the sampling system according to the invention, this advantageously has an approximately constant cross section, so that the microsamples following one another therein each flow over an axial length that is greater than at least five times the largest internal transverse dimension of these lines (e.g. their inside diameter).

According to another feature of the invention, an ancillary device may be placed on this temporary storage line, so as to inject between two successive microsamples a certain amount of fluids intended to separate these microsamples.

Thus, the installation according to the invention makes it possible in particular to carry out, automatically (i.e. without any manual intervention), a sequence of two functions, both automated, consisting firstly in taking microsamples—preferably blood microsamples—which are in discrete packets temporarily and spatially (these being readily separable for example by a break in the corresponding microtube line) and, secondly, in spatially separating, in each microsample, at least one of the phases of the liquid so as to subject it to a differentiated action, in particular for the purpose of measuring the entry function for nuclear imaging in small mammals.

It should be noted that the small size of the animals that are preferably used for taking the microsamples requires the total volume of these microsamples to be limited to an amount that is not only compatible with the health of the animal but also with its metabolism being disturbed as little as possible.

According to another optional feature of the invention, said automated installation further includes a counting device for counting, with improved sensitivity, elementary particles emitted by the microsamples, this counting device including a line for transferring these microsamples and, placed to the outside of the line, means for detecting these particles, said particles being attenuated by a wall of the line and/or by the microsamples.

According to the invention, this counting device includes at least a counting portion of oblong cross section that joins together two adjacent portions of this line, having a larger flow section and which has an [internal height (h)/internal width (l)] ratio of 20% or less, in which the internal height and internal width represent the smallest and largest transverse dimensions, respectively, of the portion, this being measured along two approximately perpendicular directions, said detection means extending transversely to this portion facing its entire width and on either side thereof.

It will be noted that if the particles to be counted are electrons or positrons, this extremely flattened geometry of the counting portion, combined with its relatively large internal width, facing which said detection means are placed so as to overhang, ensures a very high counting efficiency, typically greater than 50%, both for radiotracers based on $^{18}$F and $^{11}$C, thus allowing measurements to be taken even on blood microsamples having a volume of less than 10 µl (typically taken from mice) and possibly containing short-lived radiotracers (such as $^{11}$C).

In particular, it should be noted that this arrangement of said detection means both facing and overhanging the transverse width of the counting portion makes it possible to maximize the geometric acceptance of the detection means (by optimizing the "capture" of the particles to be counted), thus helping to improve this counting efficiency.

The term "flow section" is understood in the present description to mean the internal cross section of the counting portion (of oblong or flattened shape) and that of each of the two (preferably circular) portions adjacent this counting portion.

Preferably, this counting portion has an [internal height (h)/internal width (l)] ratio of between 5% and 10%.

Advantageously, the ratio of the flow section of the portion to that of each adjacent portion may be equal to 35% or less, and even more advantageously less than 25%.

Also advantageously, said internal height of the counting portion may be less than 20% of the inside diameter of each of the adjacent cylindrical portions and said internal width of this portion may be 1.3 times greater than this inside diameter.

According to a preferred embodiment of the invention, this counting portion has an approximately rectangular cross section, the long sides and/or the short sides of which are curved with mutually symmetrical curvatures, so that this portion has at least in part an approximately convex or concave external face.

According to another preferred feature of the invention, said line is suitable for the flow of blood microsamples, said internal height of the counting portion being between 100 µm and 250 µm and said internal width of this portion being greater than 1.3 mm, whereas the or each adjacent cylindrical portion has a diameter of between 0.8 and 1.2 mm.

Even more preferably, the area of the flow section of said counting portion is between 0.15 mm$^2$ and 0.25 mm$^2$ and this portion may then have a length of between 30 mm and 40 mm so as to be able to contain a blood microsample of about 8 µl facing said detection means.

Specifically, when the particles to be counted are electrons or positrons coming from the beta-radioactive radiation emitted by the microsamples, said counting portion advantageously has a wall thickness e, expressed in µm, and a density d, expressed in g/cm$^3$, the product e×d of which is less than 100 and preferably less than 50, in such a way that the attenuation of the particles to be counted by this portion is minimized.

According to another advantageous feature of the invention, which relates in particular to such particles of the electron or positron type, said counting portion is based on a thermoformed polymer having a density of 1.5 g/cm$^3$ or less, preferably a polyimide of the "Kapton" brand, and this portion has a wall thickness of less than 50 µm and preferably less than 30 µm.

It should be noted that this selection of such a polyimide of the "Kapton" type makes it possible to obtain this very low value of the aforementioned product e×d, compared with the usual values of this product that are generally between 150 and 200 for the known lines made of LDPE, which have a lower density than this "Kapton" polyimide but a very substantially greater thickness.

According to another feature of the invention, said detection means advantageously comprise two sets of detectors placed respectively against or in the immediate vicinity of two approximately planar large faces of said counting portion, which faces are separated from each other by said height and are joined together by two small faces of this portion, these sets of detectors extending beyond said small faces in the direction of said width so as to maximize the geometric acceptance of the latter.

According to another feature of the invention, said large faces of the counting portion each have, on their external side, a shape that is advantageously slightly convex, this being particularly well adapted to the variable pressure inherent in successive suctions of the microsamples taken via said peristaltic pump.

According to another feature of the invention, the installation according to the invention may be used to measure entry functions of mammals for nuclear imaging, in particular for quantitative imaging of tracers using PET (positron emission tomography), each liquid microsample being blood from this mammal, which is advantageously a rat or a mouse, each microsample then having a volume of 30 µl or less.

BRIEF DESCRIPTION OF THE DRAWINGS

The above features of the present invention, together with others, will be more clearly understood on reading the following description of several exemplary embodiments of the invention, given by way of nonlimiting illustration, said description referring to the appended drawings in which.

DETAILED DESCRIPTION

Figure 1:
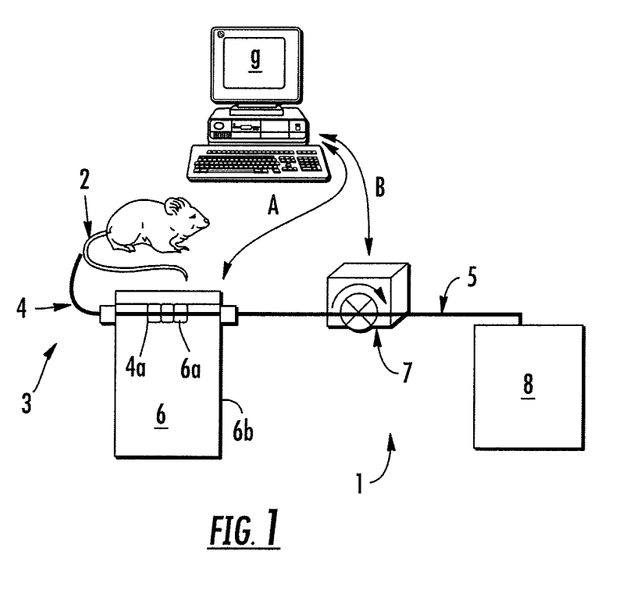
FIG. 1 is a schematic partial view of an automated sampling and measurement system according to the invention, including a device for counting particles such as beta-particles, placed upstream of a sample treatment device for the microsamples taken.

FIG. 1 illustrates by way of example an automated installation 1 for carrying out, in succession and continuously, the taking of blood microsamples from a small mammal 2, for example of the rat or mouse type, for temporarily storing said microsamples and for carrying out measurements thereof, by means of a sampling system 3 that includes a succession of lines 4 and 5 of the flexible capillary or microtube type. This sampling system 3 essentially comprises:

- a catheter 21 which is equipped with a connection device 20 (both being visible in FIG. 3) and is intended for sucking out, in bursts, the same amount of blood to be taken, via a peristaltic pump 7 which is of the peristaltic type in view of this application;
- a counting system 6 for counting the particles present in the microsamples taken, which in this example is a beta-particle counter 6 in the case of whole blood microsamples and which is placed as close as possible to the sampling point, being virtually in contact with a measurement portion 4a of this succession of lines 4, 5 (as explained below, this portion 4a has shape and material characteristics that are optimized for this counting and is centered with respect to the detection diodes 6a that the counter 6 comprises);
- a sample treatment system 8 placed downstream of the peristaltic pump 7, where these microsamples taken and analyzed are stored and treated; and
- a computer-aided control device 9 for controlling the entire system 3, including this pump 7 (see the double arrows A and B in FIG. 1 for this control).

According to the invention, the succession of lines 4 and 5 is such that the enlargements in their cross section present along these lines are always less than or equal to 20% in terms of area ratios so that the microsamples following one another in this succession of lines 4 and 5 undergo practically no mixing together therein by diffusion. In this way, these microsamples are in discrete packets spatially and temporally.

Figure 3:
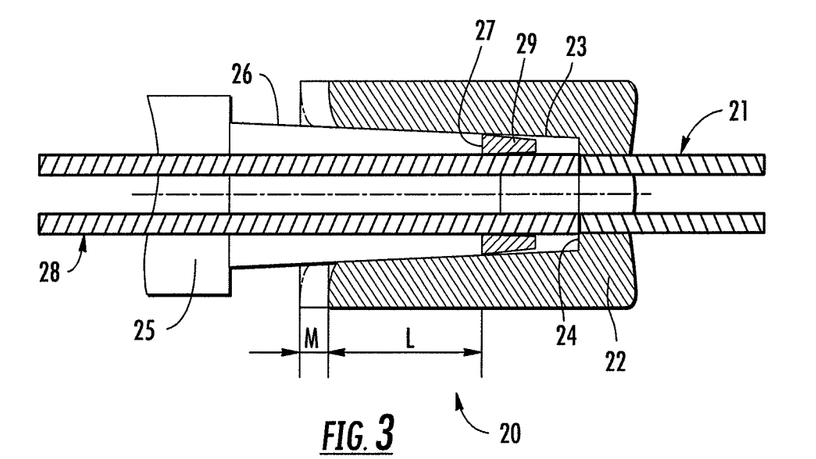
FIG. 3 is a partial view in radial section of a connection device with male and female connectors according to the invention, which is intended to be connected to this catheter and which forms part of the sampling system of FIG. 1.

As illustrated in FIG. 3, the connection device 20 according to the invention comprises, connected to the flexible catheter 21 intended to be implanted into the caudal vein of the mammal 2 and having for example an outside diameter of 1.5 mm and an inside diameter of 0.8 mm:

- a female fluid connector 22 into which the catheter 21 is pushed, said connector having a conical internal fitting surface 23 converging on a female radial end 24 into which the catheter 21 opens;
- a male fluid connector 25 which is fitted into the female connector 22 via its conical external surface 26 having the same conicity as this internal surface 23 of the female connector 22 and which converges on a male radial end 27; and
- a flexible microtube 28 made for example of LDPE (low-density polyethylene, such as an "LDPE 50" or an "LDPE 100") suitable for conveying the microsamples taken into a storage container, said microsamples being in discrete packets in space and in time, said microtube being pushed right into the male connector 25 axially beyond the male end 27 and so as to be immediately adjacent the facing female end 24 so as to minimize the localized dead volume inside the female connector 22 between these two respective ends 27 and 24.

More precisely, these connectors 22 and 25 are "Luer" connectors as defined by the ISO 59461 standard of 1986 or "Luer-lock" connectors as defined by the ISO 594-2 standard of 1998.

Preferably, the microtube 28 passes beyond the male end 27 by an axial length that is at least equal to the minimum distance d1 separating the ends 27 and 24 when the male connector 25 is pushed into the connection position in the female connector 22 in accordance with one or other of these standards. In fact, and as illustrated in FIG. 3, this microtube 28 bears in a sealed manner against the female end 24.

Figure 2:
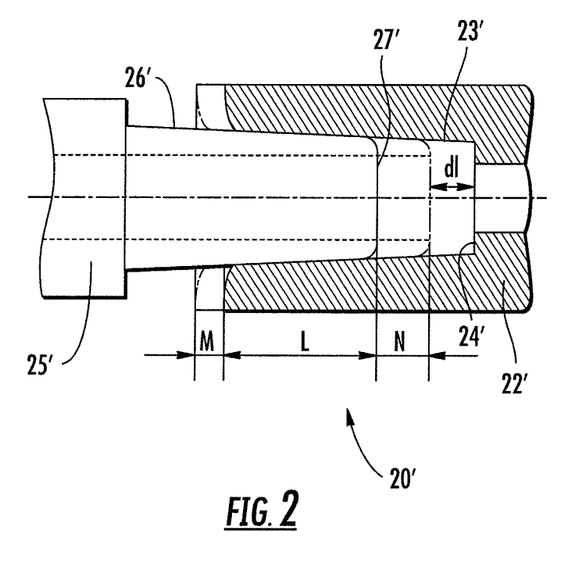
FIG. 2 is a partial view in radial section of a connection device with male and female connectors of known type, which is intended to be connected, on one side, to a catheter and, on the other side, to a flexible microtube for taking the microsamples.

The male connector 25 according to the invention makes it possible to overcome the dead volume inherent in the aforementioned length difference d1 when referring to the known connection devices illustrated in FIG. 2.

As illustrated in this FIG. 3, the microtube 28 of the invention is provided, at its free end adjacent the catheter 21, with a stiffening ring 29 mounted between the cylindrical wall of the microtube 28 and the internal surface 23 of the female connector 22. Advantageously, the stiffening means 29 is formed by a ring made of a material having a stiffness at least equal to and preferably greater than that of the microtube 28 and capable of being fastened thereto, it being possible for this fastening to be direct or via the male connector 25. In the latter case, the male connector 25 is necessarily fastened to the microtube 28.

According to a preferred variant, the ring 29 is fastened to the end of the microtube 28 and may be based on a polymeric resin. This ring 28 may be attached around the microtube 28 or else coextruded with the latter.

The connection device 20 according to the invention is produced from a device 20' of the prior art by drilling an orifice of annular cross section therein, so as to forcibly introduce the microtube 28 thereinto (the sharp cut at the end being perpendicular to the axis of the microtube 28).

It should be noted that the male connector 25 according to the invention is thus compatible with the entire range of standard female Luer devices according to the aforementioned standards and advantageously makes it possible to eliminate the dead volume in the connection device 20 (this dead volume possibly corresponding to a 20% increase in cross section relative to the minimum cross section of the line) and, consequently, to transfer, particularly blood microsamples, without any risk of them becoming mixed (and therefore with perfect traceability, the samples leaving the line being in accordance with those entering the line). Furthermore, this arrangement avoids having to wait for an excessively large number of microsamples to be taken in order to start the measurements or analyses, and also prevents a liquid volume corresponding to the dead volume being wasted.

Figure 4:
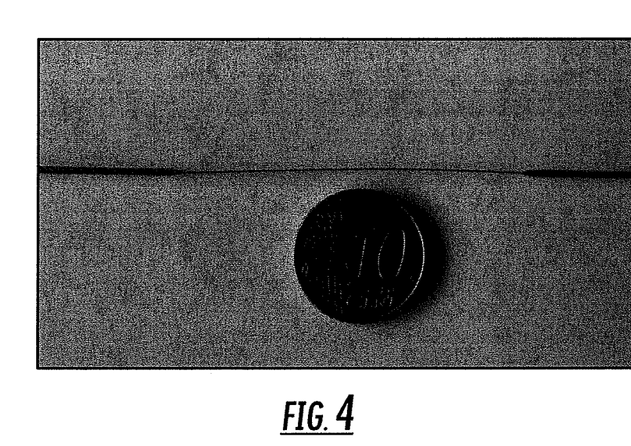
FIG. 4 is a photograph illustrating the shape and relative dimensions, in comparison with a euro 10 cent piece, of a line of this sampling and measurement system including a flattened portion of the counting device of FIG. 1, which is capable of optimizing this particle counting.
Figure 4A:
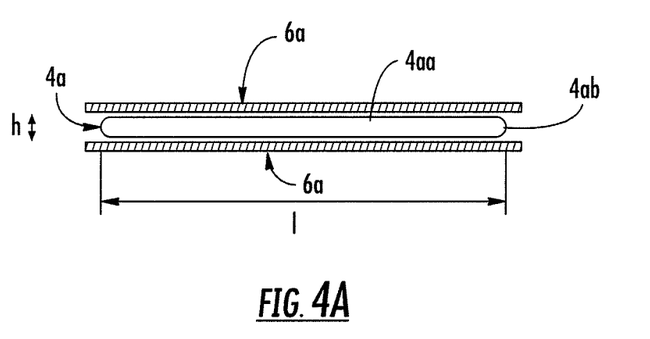
FIG. 4a is a schematic view in cross section of this flattened portion according to the invention, equipped with two sets of detectors illustrated in FIG. 1.

As illustrated in FIGS. 4 and 4a, a flattened counting portion 4a is provided in the succession of sampling lines 4, 5 according to the invention, which flattened portion joins together two cylindrical portions and is designed to optimize the particle counting by the device 6 of FIG. 1 (such as a beta counter, advantageously used for measuring the entry function of the small mammal 2). In this way it has been chosen to reduce the detection volume and to increase the counting efficiency.

For this purpose, said flattened portion 4a of oblong cross section is produced by thermoforming and is preferably made of a polyimide of the "Kapton" brand (having a density of 1.42 g/cm$^3$ and a wall thickness of 25 µm±10%), which portion links together two cylindrical microtubes, for example made of LDPE (low-density polyethylene), having an internal diameter for example of about 1 mm. As illustrated in FIG. 4a, the detection diodes 6a of the counting device 6 are arranged on either side of the external faces of the long sides 4aa of the portion 4a relative to its smallest transverse dimension, consisting here of its height h.

In this exemplary embodiment, the flattened portion 4a has an approximately rectangular cross section, the external faces of the short sides 4ab of which are curved with mutually symmetrical convex curvatures, and this portion has an [internal height h/internal width l] ratio of about 8%, where the internal height and the internal width are equal to 130 µm and 1490 µm respectively.

As regards the area ratio of the flow cross section of the flattened portion 4a—about 0.1937 mm$^2$—to that of each adjacent cylindrical portion (with an internal cross section of about 0.785 mm$^2$), this is slightly less than 25%.

Furthermore, the flattened portion 4a has a wall thickness e and a density d, the product e×d of which is approximately equal to 35.5 (with e=25 µm and d=1.42 g/cm$^3$), this being very much less than the values normally used, which are generally between 150 and 200 in the case of microlines made of LDPE (which have a lower density than that of "Kapton", but a substantially greater thickness), in such a way that the attenuation by this portion 4a according to the invention of the particles to be counted, such as electrons or beta-particles, is considerably minimized.

As illustrated in FIG. 4a, the flattened portion 4a is equipped, facing its large faces 4aa—which preferably are slightly convex—and overhanging its small faces 4ab, with two sets of said detection diodes 6a capable of counting said particles in each liquid microsample flowing therein (this overhang of the diodes 6a makes it possible to optimize their geometric acceptance, and therefore "capture" of the particles to be counted).

The thermoforming process used to obtain this flattened portion 4a according to the invention comprises in particular the following steps:
 the portion 4a is placed, cold, in the forming mold;
 its two ends are connected to flexible microtubes for pressurization;
 pressure (1.5 bar of relative pressure) is applied;
 the mold is heated to 300° C. for 15 minutes;
 the mold is cooled under pressure; and
 the pressure is slowly lowered after cooling.

What is thus obtained by this thermoforming is a flattened counting portion 4a, the large faces 4aa of which each have an area of about 1.5 mm×35 mm, i.e. 52.5 mm$^2$, thereby minimizing the thickness of liquid that the positrons or electrons have to pass through in order to reach the detectors 6a.

Figure 5:
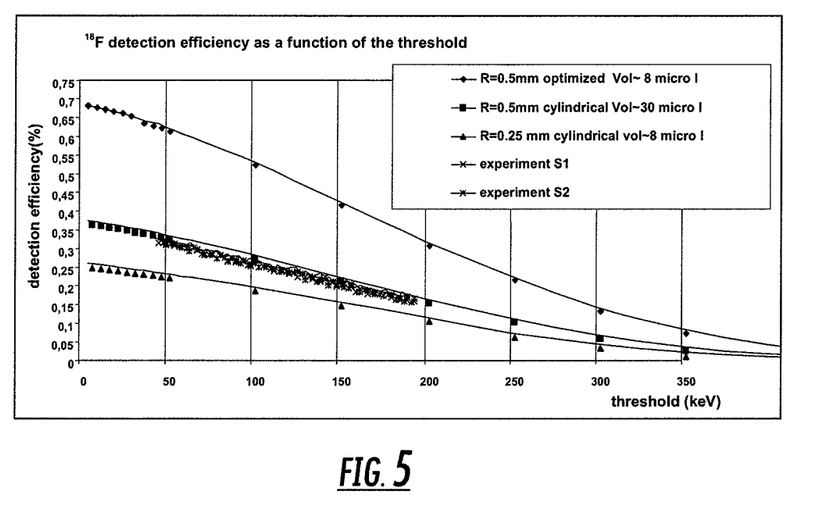
FIG. 5 is a graph illustrating the $^{18}$F radiotracer detection efficiency as a function of the detection threshold, for three types of sampling lines that include this flattened counting portion according to the invention and, for comparative trials, two cylindrical microtubes.

The graph of FIG. 5 illustrates, in the form of simulation curves confirmed by experiment, the counting efficiency results obtained for two series of experiments S1 and S2, each carried out:
 with a line according to the invention of 0.5 mm radius for the cylindrical portions and incorporating this flattened portion 4a, with an 8 µl blood microsample volume taken (compatible with a mouse);
 with a first "control" line cylindrical over its entire length (i.e. with no flattened portion) having a radius of 0.5 mm and with a 30 µl blood microsample volume taken (compatible with a rat); and
 with a second "control" line cylindrical over its entire length (i.e. with no flattened portion) having a radius of 0.25 mm, with an 8 µl blood microsample volume taken.

Thanks to this flattened portion 4a, it may be noted that the positron detection efficiency increases, going from 32% with the cylindrical microtubes to more than 60% with the microtube of the invention, for the minimum threshold (approximately 46 keV). The gain is even greater as a cylindrical microtube line compatible with an 8 µl sample would give an efficiency of about 25%. The optimized microtube according to the invention thus makes it possible to work with 8 µl samples, achieving more than 60% efficiency at the minimum threshold, compared with only 25% with a microtube entirely cylindrical over its length. This makes the sampling system 3 according to the invention particularly well suited for measuring the entry function of a mouse.

The device and the beta-particle counting method used in relation with the automated sampling system 3 will now be described in greater detail in relation to FIG. 1.

A few centimeters downstream of the first sampling line 4, each microsample passes as close as possible to the beta-particle counter 6, for which the wall thickness of the line causes only a very slight attenuation. The flattened portion 4a, fixed in the box 6b of the counter 6, makes it possible to minimize the amount of positron annihilation in the walls, and its geometry is such that it can contain the volume of a sample (either 30 µl or 8 µl) correctly centered beneath the six silicon detection diodes (measuring 10×10×0.3 mm$^3$) surrounding the portion 4a, as illustrated in FIG. 1. These diodes 6a are themselves surrounded by a lead shield 2 cm in thickness intended to eliminate the physical noise coming from the photons emanating from the animal 2. The rest of this measurement system 6 comprises an electronic processing/interfacing card, making the whole system compact and robust, being in the form of a box 6b of small dimensions (8×10×4 cm$^3$).

It is advantageous, in order to minimize the probability of annihilation in the blood of a positron coming from the beta radioactivity, to give the flexible microtube the flattened shape of the portion 4a, at least at the point where it passes in front of the diodes 6a. Moreover, as explained above, this geometric configuration also ensures that the liquid is spread out as a thin sheet, thereby increasing the area of liquid facing the detecting surfaces. The configuration adopted for the measurement system 6 is as follows.

The flattened portion 4a, with a wall thickness of 25 µm, is sandwiched between the diodes 6a, with a thickness of 0.3 mm (three diodes 6a at the top and three others at the bottom).

The read-out electronics for these diodes 6a and the electronics controlling the data acquisition and transfer have been integrated into a single electronic module, which has been optimized so as to reduce as far as possible the electronic noise, allowing the detection threshold to be minimized for optimum efficiency.

The "front-end" electronics (shaper and discriminator) is provided by an ASIC (comprising 16 channels, a common threshold, 16 outputs+1 OR). The threshold can be adjusted by the user. The acquisition card is a configurable USB test card benefiting from the flexibility of the USB interface of personal computers and from the progress made in FPGA (Field Programmable Gate Array) configurable digital circuits. This allows a large number of signals to be rapidly processed and can be programmed from the interface of a computer.

The basic scheme is illustrated in FIG. 1. The sampling line 4 is extended by the flattened portion 4a, which takes over inside the box 6b, the blood emerging on the other side of the latter. This blood flow is performed by the peristaltic pump 7. The volume of the microsamples taken can be adjusted, as can their sampling times. These parameters are controlled by the computer of the control device 9 of the installation 1.

The minimum time between two microsamplings is 1 second. To cover the dynamic range of the kinetics of the radiotracer in the blood, the microsamples are taken every second after the injection for about 30 seconds to 1 minute, and then they are taken at more spaced apart time intervals, the slope of the curve being more gentle during this phase.

The connections between the various lines and the box 6b are designed to avoid any loss of volume of the microsamples and any diffusion between two adjacent microsamples.

These blood microsamples are thus taken in discrete packets spatially and temporally and they thus progress without diffusion as far as the sample treatment system 8 where they are stored and advantageously subjected to the extraction of at least one of their phases or of their components, implemented by centrifugation as will be described below with reference to FIGS. 6a, 6b and 7.

Figure 6A:
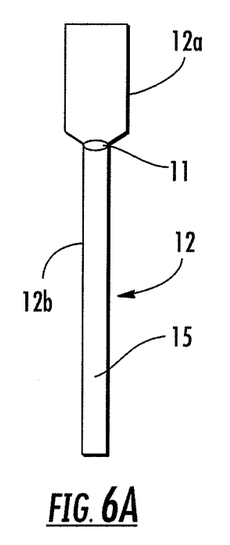
FIGS. 6a and 6b are two schematic longitudinal sectional views illustrating the shape and the content of a microholder according to the invention filled with a whole-blood-based microsample before and after centrifugation, respectively.
Figure 6B:
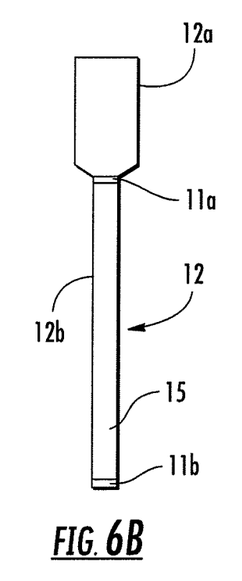

As illustrated in FIGS. 6a and 6b, the continuous automated extraction system 10 of the installation 1 according to the invention, downstream of the sampling system 3 and the peristaltic pump 7, is intended to separate, inside each liquid microsample 11, one of the phases 11a or one of the components having a significantly different density from the remainder 11b of the microsample, via a centrifugation carried out in microholders 12 each having a filling upper portion 12a and a separating lower portion 12b.

The microsamples 11 arrive one after another spatially in the line for temporarily storing the samples, adjacent the sampling system 8 visible in FIG. 1. At the downstream end of this storage line, each microsample 11 drops into a receptacle where it is taken up by a micropipette (see FIGS. 8-11, reference numeral 18), which is mounted on an articulated arm (see FIGS. 8-11, reference numeral 19) and is adapted to the flared end of this line, the synchronism between these actions and the progression of the microsamples 11 in this storage line being controlled by the computer-aided control device 9.

Figure 7:
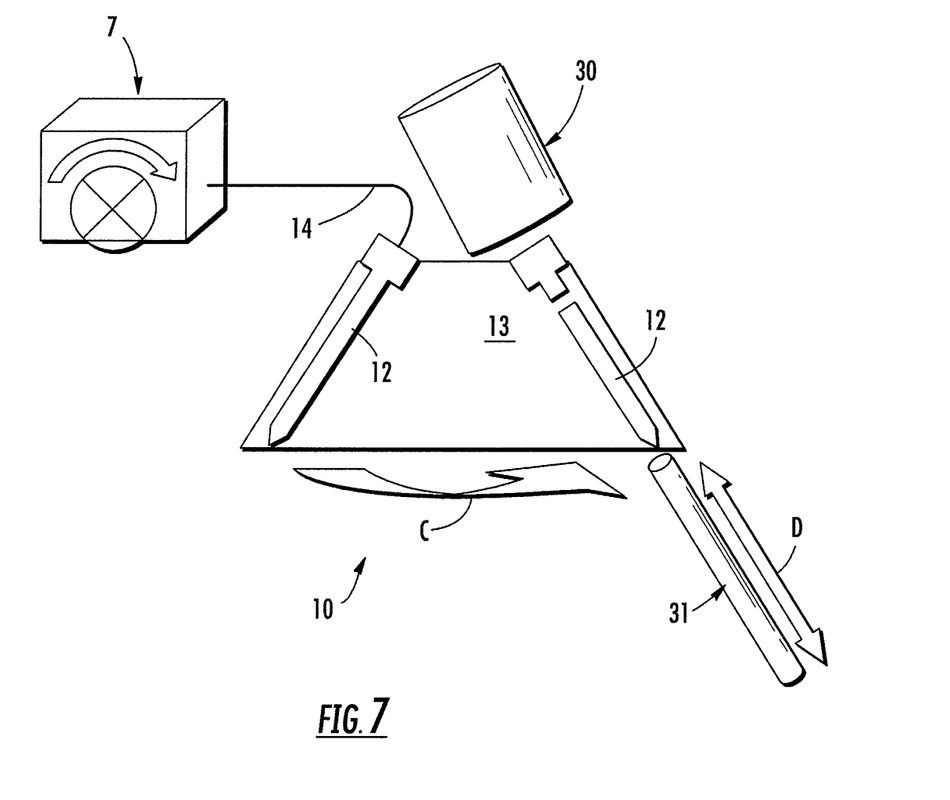
FIG. 7 is a schematic view of an automated extraction system according to the invention, which is provided at its outlet with a measurement system according to the invention, formed for example by a well-type gamma counter.
Figure 8:
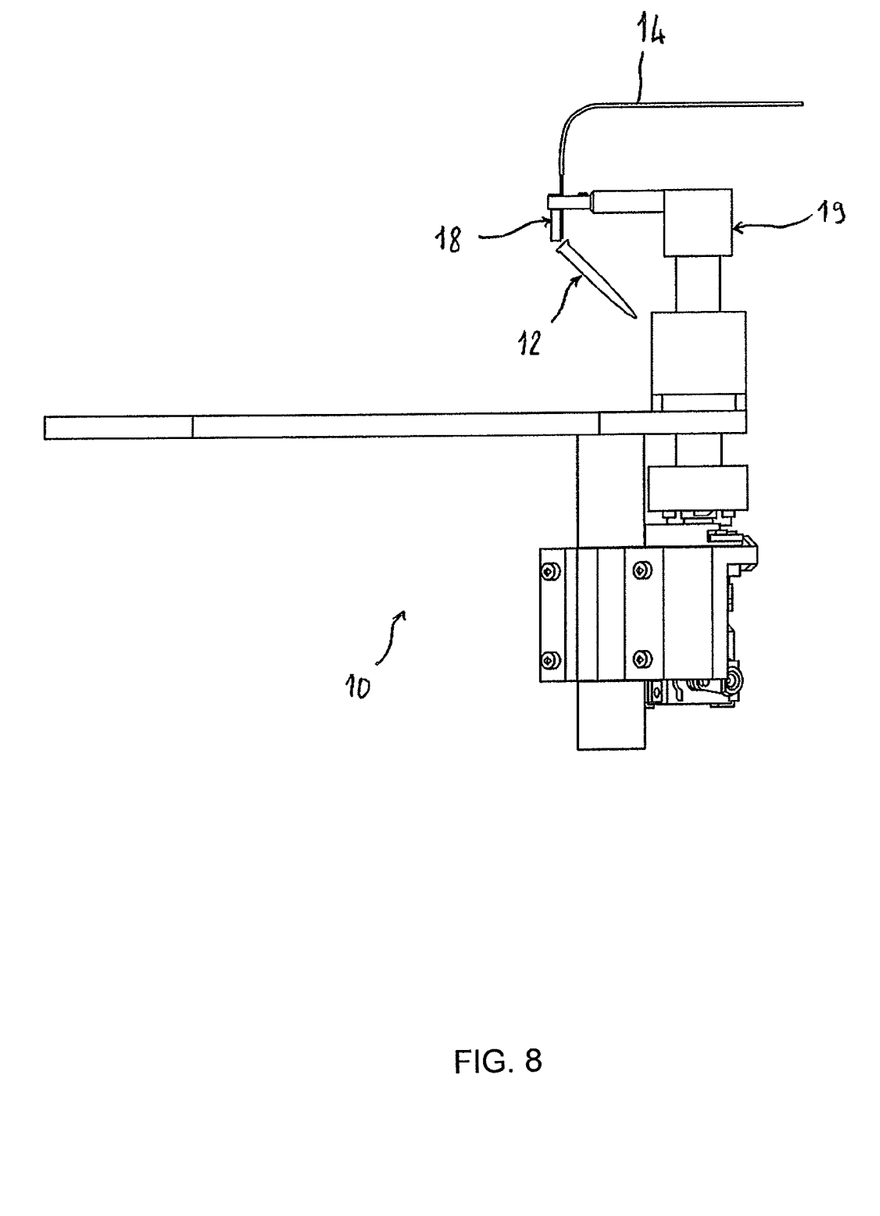
FIG. 8 is a schematic view of an automated extraction system according to an embodiment of the invention.
Figure 9:
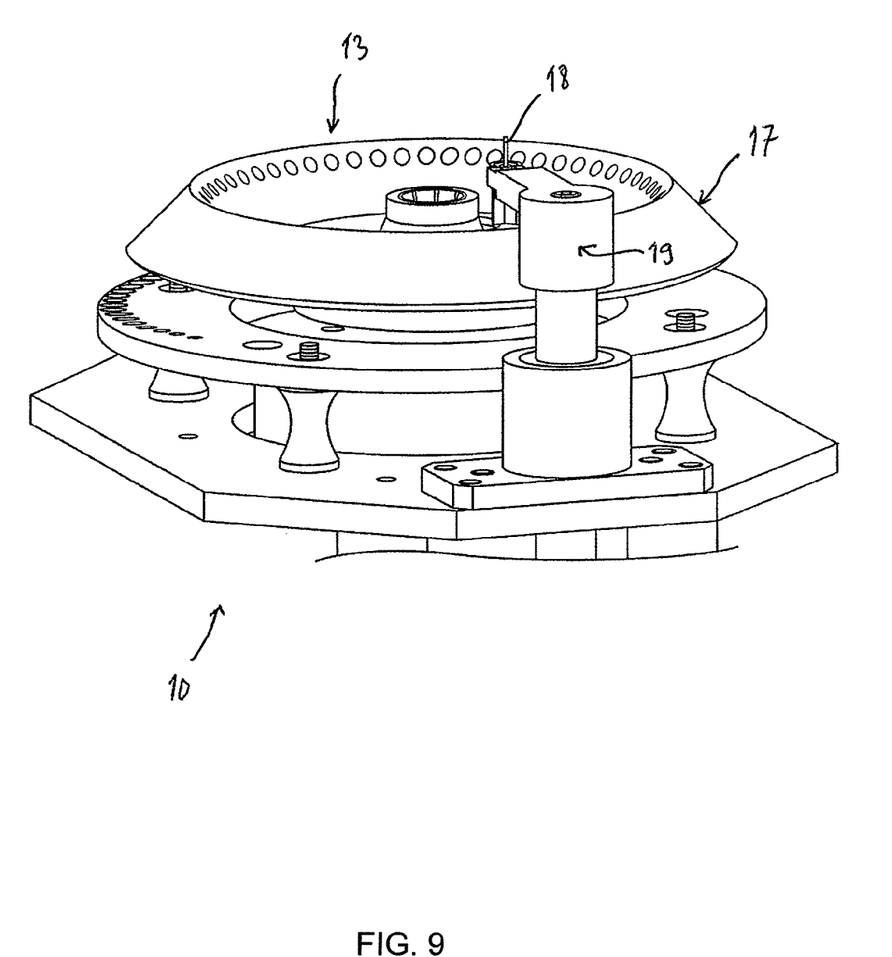
FIG. 9 is a perspective view of an automated sampling and measurement system according to the invention, including an actuating member.
Figure 10:
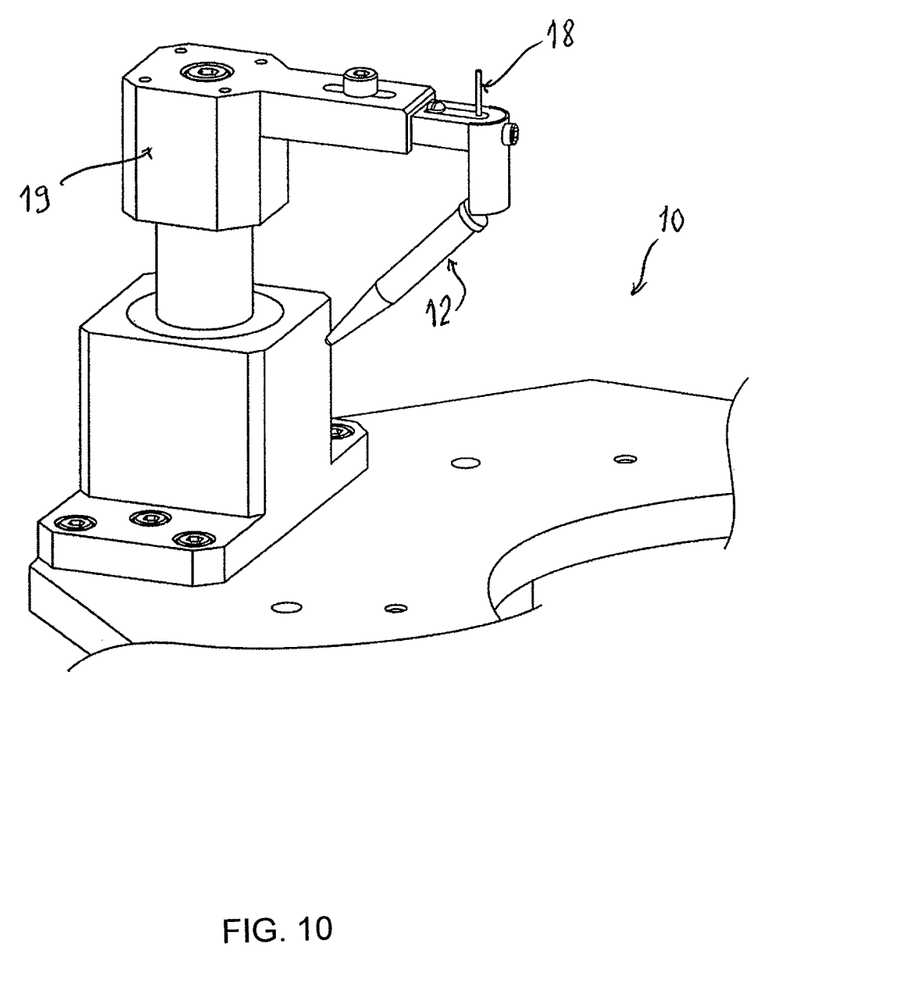
FIG. 10 is a partial perspective view of an automated sampling and measurement system according to the invention, including an articulated arm on which a micropipette is movably mounted.
Figure 11:
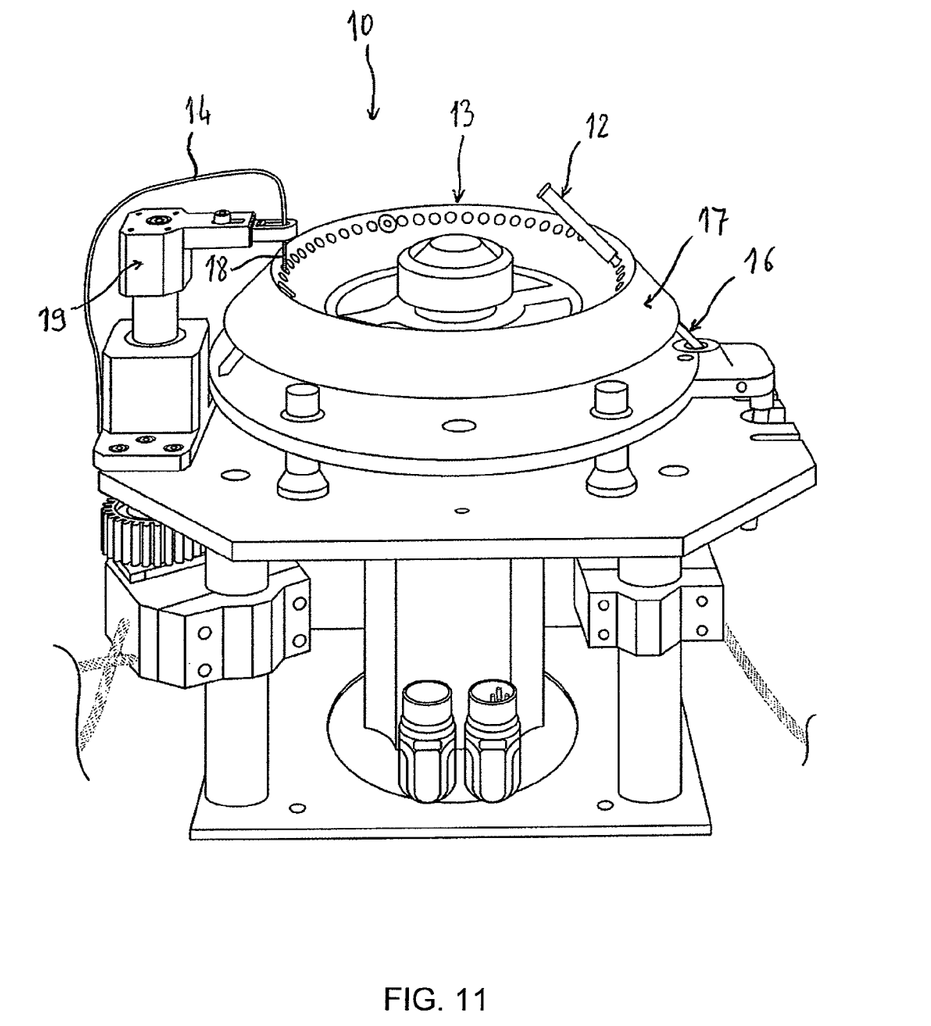
FIG. 11 is a perspective view of an automated sampling and measurement system according to the invention, including an actuating member on which a micropipette is movably mounted and that also depicts an ejecting means.

As illustrated in FIG. 7, this micropipette successively transfers the microsamples 11 thus taken into specific microholders 12 designed to accommodate them (the volume of each microsample 11 being between 1 µl and 100 µl) and to rotate at high speed in a centrifuge 13, which is of the carousel type, with locations suitable for accommodating these microholders 12. This centrifuge 13 is also controlled by the computerized control device 9. Thus, the entire extraction system 10 is controlled by computer, in synchronism with the system 3 for taking the microsamples and the micropipette for transferring them.

As explained above in relation to the present invention, it should be noted that at least one or each microholder 12 filled with the corresponding microsample 11 has a mass that is more than ten times and preferably more than 100 times the mass of this microsample 11, so that it is possible to carry out, at a given instant, the extraction by centrifugation of a microsample 11 contained in only one microholder 12 or only some of the microholders 12 that may be housed in the centrifuge 13, progressively as these microholders are filled.

The extraction process carried out by means of the system 10 comprises the following succession of steps:

for at least one microholder 12 placed in a housing in the carousel of the centrifuge 13 and not yet having received a microsample, the transfer micropipette 18 takes a microsample from said receptacle and introduces it into this microholder 12;

the centrifuge 13 rotates (see arrow C) until, for each microsample 11, at least one of the components 11a, such as the plasma, has separated from the remainder 11b, in this case the blood cells (e.g. the red corpuscles), then stops; and then the ejection device (see FIG. 11, reference numeral 16) ejects the microholder or microholders that have received a microsample 11.

It should be noted that the rotor of the centrifuge 13 may also provide the function of positioning the microholders 12 in front of the filling micronozzle 14 of the centrifuge 13.

Preferably, this extraction process according to the invention includes the prior addition to each microholder 12 of an extraction agent 15 (see FIGS. 6a and 6b), the density of which is between the density of the phase of the liquid to be separated and that of the remainder of the liquid. Even more preferably within the context of blood microsamples, the density of this agent 15 is designed to be approximately equal to the median of the blood plasma density and the corpuscle density. Advantageously, a MAGIC (Methacrylic and Ascorbic acid in Gelatin Initiated by Copper) polymer gel is used as extraction agent 15 so that, during centrifugation, this agent 15 initially deposited on the bottom of each microholder 12 migrates to the interface between said phase 11a to be extracted and the remainder 11b of the microsample 11, forming thereat a physical barrier through which the phase 11b passes so as to be deposited on the bottom of the microholder 12. Thus, in the case of whole blood microsamples, only the blood cells 11b pass into the gel 15 before reaching the bottom of each microholder 12, the extracted plasma 11a remaining on the surface of the gel and the distance between plasma 11a and cells 11b then being a maximum (see FIGS. 6a and 6b).

More precisely, the following steps are carried out in succession during the centrifugation of the microholders 12:

a) each microholder 12 is filled with the gel 15, which is then located in the upper portion 12a;

b) the microholders 12 are placed in the rotor of the centrifuge 13;

c) the microholders 12 containing this gel 15 are centrifuged, said gel entirely filling the lower portion 12b;

d) a microsample is deposited in the portion 12a of each microholder 12 thus obtained; and then e) the microholders 12 are centrifuged in order to carry out the aforementioned extraction.

Steps a) and b) may be reversed without thereby departing from the scope of the invention.

According to a variant of the invention, steps a) and c) may be carried out prior to step b), optionally on another installation. In this case, the use of precentrifuged microholders 12 prefilled with gel may advantageously simplify the in-line operations. Even more advantageously, it will be possible to use a centrifuge tray filled beforehand with prefilled and precentrifuged microholders.

To minimize the time delay between taking a microsample and counting it, in terms of whole blood and plasma, and given the fact that the microsamples are taken at very unequal time intervals, it will be noted that with this extraction system according to the invention it makes no difference whether the centrifugation is carried out on a single microsample 11, a few microsamples 11 or all the microsamples that the centrifuge 13 can contain, because of the fact that the mass of each microholder 12 is not significantly modified by introducing each microsample 11. It should also be noted that adding the MAGIC extraction agent 15 before each microholder 12 is filled with a microsample 11 makes the mass of the latter even more negligible.

Thus, continuous "in line" centrifugation may be carried out progressively as each microholder 12 is filled (for example as soon as a microsample 11 has been deposited or as soon as a sufficiently long pause phase—at least one minute—occurs) independently of the charging level of the centrifuge 13, unlike the known centrifugation systems that require the microholders positioned in the centrifuge to be completely filled in order to ensure rotor balancing (i.e. no imbalance) before permitting the centrifugation phase.

As also illustrated in FIG. 7, after automated extraction of a microholder 12 from the rotor of the centrifuge 13, this centrifuged microholder may pass in front of a final measurement system 30, for measuring a physical quantity for which the wall of each microholder 12 is transparent, which here is a gamma counter of the well-counter type, carrying out gamma-counting on the plasma alone. This gamma counter 30 cooperates with a computer-controlled robotic push-rod 31, which is positioned on the other side of the centrifuge 13 and is capable of pushing (see arrow D) each microholder 12 so as to bring the upper part of the latter into a shield for this counter 30, so as to measure the activity of just the plasma 11a, the blood cells 11b deposited on the bottom of each microholder 12 by centrifugation remaining outside this shield.

In general with reference to the automated installation 1 according to the invention, it should be noted that the time delay between the instant of taking a microsample and that of its plasma counting must be minimized in order to prevent the natural radioactive decay of the radiotracer from reducing the counting statistics during the plasma counting phase. To meet this requirement, asynchronous treatment of the microsamples may be carried out, so as to allow a microsample to be conveyed from its sampling point right to the plasma separator without having to wait for the next microsample to be taken. This treatment is possible only in phases in which the sampling frequency is slow. In the rapid-frequency sampling phases, the successive microsamples are conveyed progressively as the following ones are taken. However, when microsamples are taken in a slow sequence, the automatic controller of the invention handles them in discrete packets and conveys them singly through the analysis chain.

Moreover, it should be noted that the automated installation of the invention is particularly suitable for preclinical research for quantitative imaging of new tracers in PET (Positron Emission Tomography). In this case, the liquid in question is blood and the application consists in measuring the entry function for small animals such as rats or mice. The small size of these animals, and therefore the small total amount of blood that they possess, limit the volume of each microsample to about 30 μl in the case of rats and to about 8 μl in the case of mice.

The invention claimed is:

1. A continuous automated extraction method for physically extracting at least one liquid phase of a series of liquid microsamples which each have a volume of less than 100 μL, the method comprising the steps of:
    taking the microsamples in discrete packets, both in space and in time,
    physically extracting at least one liquid phase utilizing:
        a centrifuge provided with a plurality of microholders, at least one of which contains and is filled with the corresponding liquid microsample and includes a filling upper portion that is extended by a separating lower portion of smaller cross section than that of the upper portion, the upper portion and the lower portion of at least one of the microholders each containing only one microsample having said volume;
        a peristaltic pump successively metering said liquid microsamples upstream of said centrifuge;
        a transfer device comprising a micropipette and an articulated arm actuating the micropipette, wherein the transfer device transfers, via said pump, said volume of each liquid microsample of less than 100 μL directly to at least one of the microholders waiting to be filled;
        an ejection device ejecting and positioning the microholders; and
        a computer-aided control device controlling said centrifuge, transfer device, and said ejection device so as to perform the continuous extraction method;
    filling at least one of said microholders with a liquid microsample, wherein said or each microholder thus filled has a mass which is more than ten times the mass of said microsample so that the mass of the at least one filled microholder is not substantially modified by the microsample that it contains;
    extracting by centrifugation, at a given instant, only a single microsample contained in a single microholder, or a part of the microsamples contained only in some of these microholders, progressively as the latter are filled.

2. The method of claim 1, further comprising, before each microholder is filled, incorporating into the latter of an extraction agent capable of extracting said at least one liquid phase from the microsample and the density of which is selected to be intermediate between that of said at least one liquid phase and that of a remainder of the microsample in such a way that, during the centrifugation, said agent is initially located in said upper portion and then, by centrifugation, in said lower portion of each microholder in order to migrate to an interface between said at least one liquid phase and said remainder of the microsample, forming a physical barrier thereat.

3. The method of claim 2, wherein said extraction agent comprises a MAGIC (Methacrylic and Ascorbic acid in Gelatin Initiated by Copper) polymer gel.

4. The method of claim 2, wherein the step of incorporating said extraction agent in each microholder to be filled is carried out by displacing a micropipette actuated by an articulated arm introducing, into each microholder, a specified constant amount of this agent, and then by rotation of said centrifuge until said agent falls to the bottom of this microholder.

5. The method of claim 1, further comprising, before the step of extracting, a step of transferring a specified volume of each microsample to at least one of the microholders that has not yet received a microsample, via the displacement of a micropipette mounted on an articulated arm.

6. The method of claim 5, wherein the same pipette as that for transferring said agent is used for transferring the microsamples.

7. The method of claim 1, wherein, prior to said extracting step:
   a) the microsamples are continuously taken, by an automated sampling system, according to a monotonic time function, via sending at preprogrammed instants $t_i$, by said computer-aided control device, to said sampling system, of signals for the taking of a microsample of preprogrammed volume; and then
   b) these microsamples thus taken follow one another spatially and temporally in a temporary storage line as far as a downstream end of this line where each microsample drops into a receptacle from where it is then continuously transferred, via said peristaltic pump into the microholders of said centrifuge, the synchronism between this transfer and the progression of the microsamples in said storage line being controlled by said computer-aided control device.

8. The method of claim 1, wherein said liquid microsamples are whole blood microsamples from a mammal.

9. The method of claim 1, wherein the mass of each filled microholder is more than 100 times the mass of said microsample.

10. The method of claim 1, wherein said portions of each microholder have substantially identical volumes, each volume being intended to contain in practice one microsample.

* * * * *